(12) United States Patent
Tan et al.

(10) Patent No.: US 9,795,556 B2
(45) Date of Patent: *Oct. 24, 2017

(54) COMPOSITIONS AND METHODS FOR TREATING HAIR

(71) Applicant: L'OREAL, Paris (FR)

(72) Inventors: Siliu Tan, Westfield, NJ (US); Nghi Van Nguyen, Edison, NJ (US); Jim Singer, South Orange, NJ (US); Jean-Thierry Simonnet, Mamaroneck, NY (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/931,329

(22) Filed: Jun. 28, 2013

(65) Prior Publication Data

US 2015/0004116 A1    Jan. 1, 2015

(51) Int. Cl.
    *A61Q 5/06* (2006.01)
    *A61K 8/87* (2006.01)
    *A61K 8/81* (2006.01)
    *A45D 7/06* (2006.01)

(52) U.S. Cl.
    CPC ............... *A61K 8/87* (2013.01); *A45D 7/06* (2013.01); *A61K 8/8147* (2013.01); *A61K 8/8152* (2013.01); *A61Q 5/06* (2013.01); *A61K 2800/594* (2013.01)

(58) Field of Classification Search
    None
    See application file for complete search history.

(56) References Cited

U.S. PATENT DOCUMENTS

| | | | |
|---|---|---|---|
| 3,110,695 A | 11/1963 | Ceresa | |
| 3,304,273 A | 2/1967 | Stamberger | |
| 3,383,351 A | 5/1968 | Stamberger | |
| 3,412,054 A | 11/1968 | Milligan et al. | |
| 3,523,095 A | 8/1970 | Laurito et al. | |
| 3,915,921 A | 10/1975 | Schlatzer, Jr. | |
| 4,003,699 A | 1/1977 | Rose et al. | |
| RE30,199 E | 1/1980 | Rose et al. | |
| 4,509,949 A | 4/1985 | Huang et al. | |
| 4,644,030 A | 2/1987 | Loewrigkeit et al. | |
| 4,710,374 A | 12/1987 | Grollier et al. | |
| 4,798,721 A * | 1/1989 | Yahagi ............ A61K 8/02 424/70.11 | |
| 4,985,239 A | 1/1991 | Yahagi et al. | |
| 5,061,289 A | 10/1991 | Clausen et al. | |
| 5,085,859 A | 2/1992 | Halloran et al. | |
| 5,156,911 A | 10/1992 | Stewart | |
| 5,173,526 A | 12/1992 | Vijayendran et al. | |
| 5,221,534 A | 6/1993 | DesLauriers et al. | |
| 5,380,340 A | 1/1995 | Neunhoeffer et al. | |
| 5,441,728 A | 8/1995 | Tsaur et al. | |
| 5,534,267 A | 7/1996 | Neunhoeffer et al. | |
| 5,565,216 A | 10/1996 | Cowsar et al. | |
| 5,618,523 A | 4/1997 | Zysman et al. | |
| 5,637,291 A | 6/1997 | Bara et al. | |
| 5,663,366 A | 9/1997 | Neunhoeffer et al. | |
| 5,679,327 A | 10/1997 | Darkwa et al. | |
| 5,708,151 A | 1/1998 | Moeckli | |
| 5,753,215 A | 5/1998 | Mougin et al. | |
| 5,766,576 A | 6/1998 | Loewe et al. | |
| 5,932,194 A | 8/1999 | Plessix et al. | |
| 6,013,682 A | 1/2000 | Dalle et al. | |
| 6,099,592 A | 8/2000 | Vidal et al. | |
| 6,110,451 A | 8/2000 | Matz et al. | |
| 6,120,778 A | 9/2000 | Simonnet | |
| 6,126,929 A | 10/2000 | Mougin | |
| 6,126,948 A | 10/2000 | Simonnet et al. | |
| 6,165,446 A | 12/2000 | Samain et al. | |
| 6,214,328 B1 | 4/2001 | Chang et al. | |
| 6,268,431 B1 | 7/2001 | Snyder et al. | |
| 6,284,003 B1 | 9/2001 | Rose et al. | |
| 6,338,741 B1 | 1/2002 | Vidal et al. | |
| 6,399,050 B1 | 6/2002 | Pasquet et al. | |
| 6,464,990 B2 | 10/2002 | Simonnet et al. | |
| 6,482,394 B1 | 11/2002 | Schehlmann et al. | |
| 6,585,965 B1 | 7/2003 | Carballada et al. | |
| 6,592,633 B2 | 7/2003 | Lang et al. | |
| 6,613,315 B1 | 9/2003 | Dupuis | |
| 6,645,258 B2 | 11/2003 | Vidal et al. | |
| 6,703,028 B1 | 3/2004 | Samain et al. | |
| 6,726,916 B1 | 4/2004 | Ramin | |
| 6,730,789 B1 | 5/2004 | Birault et al. | |
| 6,946,123 B2 | 9/2005 | De La Poterie et al. | |
| 7,211,244 B2 | 5/2007 | Auguste et al. | |
| 7,651,693 B2 | 1/2010 | Merlau et al. | |
| 7,740,832 B1 | 6/2010 | Rollat-Corvol et al. | |

(Continued)

FOREIGN PATENT DOCUMENTS

| | | |
|---|---|---|
| DE | 1152536 B | 8/1963 |
| DE | 2359399 A1 | 6/1975 |
| DE | 3843892 A1 | 6/1990 |
| EP | 0216479 A1 | 4/1987 |
| EP | 0874017 A2 | 10/1998 |
| EP | 0898958 A1 | 3/1999 |
| EP | 1652509 A2 | 5/2006 |
| EP | 2356981 A1 | 8/2011 |
| EP | 2570192 A1 | 3/2013 |
| FR | 2733749 A1 | 11/1996 |

(Continued)

OTHER PUBLICATIONS

English language abstract for EP 0898960 (Mar. 3, 1999).
English language abstract for EP 1082953 (Mar. 14, 2001).
English language abstract for FR 2633940 (Jul. 12, 1991).
English language abstract for FR 2834458 (Jul. 11, 2003).
English language abstract for FR 2898050 (Sep. 7, 2007).

(Continued)

*Primary Examiner* — Jyothsna Venkat

(74) *Attorney, Agent, or Firm* — The Marbury Law Group, PLLC

(57) ABSTRACT

Disclosed are hair styling compositions comprising at least two latex polymers chosen from acrylate and polyurethane polymers, wherein at least one latex polymer is a film-forming polymer, and at least one component chosen from thickening agents. Methods of styling the hair are also disclosed.

19 Claims, No Drawings

(56) References Cited

U.S. PATENT DOCUMENTS

| | | | |
|---|---|---|---|
| 7,785,613 | B2 | 8/2010 | Collin et al. |
| 7,993,632 | B2 | 8/2011 | Lezer et al. |
| 8,343,238 | B1 | 1/2013 | Lopez et al. |
| 8,398,961 | B2 | 3/2013 | Kaplan et al. |
| 8,691,200 | B2 | 4/2014 | Vilbert |
| 8,865,147 | B2 | 10/2014 | Rizk et al. |
| 2002/0007521 | A1 | 1/2002 | Lang et al. |
| 2002/0010970 | A1 | 1/2002 | Cottard et al. |
| 2002/0022009 | A1 | 2/2002 | De La Poterie et al. |
| 2002/0050013 | A1 | 5/2002 | Vidal et al. |
| 2002/0055562 | A1 | 5/2002 | Butuc |
| 2002/0187116 | A1* | 12/2002 | De La Poterie ......... A61Q 1/10 424/63 |
| 2002/0198328 | A1 | 12/2002 | L'Alloret |
| 2003/0019051 | A9 | 1/2003 | Vidal et al. |
| 2003/0026815 | A1 | 2/2003 | Scott et al. |
| 2003/0044440 | A1 | 3/2003 | Toumi |
| 2003/0053976 | A1 | 3/2003 | Tournilhac et al. |
| 2003/0059377 | A1 | 3/2003 | Riley |
| 2003/0059388 | A1 | 3/2003 | Auguste et al. |
| 2003/0064045 | A1 | 4/2003 | Tournilhac et al. |
| 2003/0103927 | A1 | 6/2003 | Maubru |
| 2003/0138465 | A9 | 7/2003 | Douin et al. |
| 2003/0147832 | A1 | 8/2003 | L'Alloret |
| 2003/0161804 | A1 | 8/2003 | Perron et al. |
| 2004/0071646 | A1 | 4/2004 | Pataut et al. |
| 2004/0096474 | A1 | 5/2004 | Merlau et al. |
| 2004/0214913 | A1 | 10/2004 | L'Alloret |
| 2005/0008605 | A1 | 1/2005 | L'Alloret |
| 2005/0020779 | A1 | 1/2005 | Mougin et al. |
| 2005/0025736 | A1 | 2/2005 | Jachowicz et al. |
| 2005/0048016 | A1 | 3/2005 | Lebreton et al. |
| 2005/0053568 | A1 | 3/2005 | Aubrun-Sonneville Odile et al. |
| 2005/0065253 | A1 | 3/2005 | Collin et al. |
| 2005/0089490 | A1 | 4/2005 | Jachowicz et al. |
| 2006/0115446 | A1 | 6/2006 | Rollat-Corvol et al. |
| 2006/0134043 | A1 | 6/2006 | Nakamura |
| 2006/0182702 | A1 | 8/2006 | Lazzeri et al. |
| 2006/0292095 | A1 | 12/2006 | Biatry et al. |
| 2007/0031361 | A1 | 2/2007 | Herrmann et al. |
| 2007/0190008 | A1* | 8/2007 | Campain et al. ............ 424/70.2 |
| 2007/0224140 | A1 | 9/2007 | Quadir et al. |
| 2007/0286833 | A1 | 12/2007 | Keller et al. |
| 2008/0138307 | A1 | 6/2008 | Bazemore et al. |
| 2008/0175808 | A1 | 7/2008 | Pavel |
| 2008/0305064 | A1* | 12/2008 | Bui et al. ................. 424/70.121 |
| 2009/0035335 | A1 | 2/2009 | Marotta et al. |
| 2009/0060858 | A1 | 3/2009 | Schwarzwaelder et al. |
| 2009/0074695 | A1 | 3/2009 | Mahe et al. |
| 2009/0280076 | A1 | 11/2009 | Yoshida et al. |
| 2009/0297467 | A1 | 12/2009 | Laurent et al. |
| 2009/0317432 | A1 | 12/2009 | Kergosien |
| 2010/0028284 | A1 | 2/2010 | Atis et al. |
| 2010/0119467 | A1 | 5/2010 | Dumousseaux et al. |
| 2010/0189678 | A1* | 7/2010 | Knappe et al. ............ 424/70.16 |
| 2010/0278770 | A1 | 11/2010 | Arditty et al. |
| 2011/0014139 | A1 | 1/2011 | Viala et al. |
| 2011/0015279 | A1 | 1/2011 | Doerr et al. |
| 2011/0097289 | A1 | 4/2011 | Viala et al. |
| 2011/0097293 | A1 | 4/2011 | Grey et al. |
| 2011/0142780 | A1* | 6/2011 | Hentrich .............. A61K 8/8182 424/70.19 |
| 2011/0150802 | A1 | 6/2011 | Bui et al. |
| 2011/0150807 | A1* | 6/2011 | Bui et al. ..................... 424/70.7 |
| 2012/0247500 | A1 | 10/2012 | Plos et al. |
| 2012/0282309 | A1 | 11/2012 | Dihora et al. |
| 2012/0308496 | A1 | 12/2012 | Viala et al. |
| 2013/0084256 | A1 | 4/2013 | Li et al. |
| 2013/0167863 | A1 | 7/2013 | Schmelz et al. |
| 2013/0171084 | A1 | 7/2013 | Kawaratani et al. |
| 2013/0284198 | A1 | 10/2013 | Rizk et al. |
| 2014/0102468 | A1 | 4/2014 | Pistorio et al. |
| 2014/0105845 | A1 | 4/2014 | Bui et al. |
| 2014/0105945 | A1 | 4/2014 | Bui et al. |
| 2014/0186270 | A1 | 7/2014 | Suleiman et al. |
| 2015/0004119 | A1 | 1/2015 | Tan et al. |

FOREIGN PATENT DOCUMENTS

| | | | |
|---|---|---|---|
| FR | 2774899 | A1 | 8/1999 |
| FR | 2889943 | A1 | 3/2007 |
| GB | 1026978 | A | 4/1966 |
| GB | 1040452 | A | 8/1966 |
| GB | 1153196 | A | 5/1969 |
| WO | 9515144 | A1 | 6/1995 |
| WO | 0119333 | A1 | 3/2001 |
| WO | 2005100444 | A1 | 10/2005 |
| WO | 2007/102972 | A1 | 9/2007 |
| WO | 2010133658 | A2 | 11/2010 |
| WO | 2011056332 | A1 | 5/2011 |
| WO | 2011137338 | A2 | 11/2011 |
| WO | 2012/072774 | A1 | 6/2012 |
| WO | 2013059106 | A1 | 4/2013 |
| WO | 2013074210 | A1 | 5/2013 |
| WO | 2013092378 | A1 | 6/2013 |
| WO | 2013092379 | A1 | 6/2013 |
| WO | 2013092380 | A1 | 6/2013 |
| WO | 2013092381 | A1 | 6/2013 |
| WO | 2013092382 | A1 | 6/2013 |
| WO | 2013092562 | A1 | 6/2013 |
| WO | 2013092788 | A1 | 6/2013 |
| WO | 2014001390 | A1 | 1/2014 |
| WO | 2014001391 | A1 | 1/2014 |
| WO | 2014/058856 | A1 | 4/2014 |
| WO | 2014/062334 | A1 | 4/2014 |
| WO | 2014124066 | A1 | 8/2014 |

OTHER PUBLICATIONS

English language abstract for FR 2968978 (Jun. 22, 2012).

Galgoci, Ernest C., et al., "Solvent-Free Urethane-Acrylic Hybrid Polymers for Coatings," JCT Coatings Tech, 2(13), Feb. 2005, pp. 28-36.

Jachowicz, J., et al., "Mechanical Analysis of Elasticity and Flexibility of Virgin and Polymer-Treated Hair Fiber Assemblies," J. Cosmet. Sci., 53, Nov./Dec. 2002, pp. 345-361.

Co-pending U.S. Appl. No. 13/931,187; Siliu Tan et al., "Compositions and Methods for Treating Hair," filed Jun. 28, 2013.

Co-pending U.S. Appl. No. 13/931,204; Siliu Tan et al., "Compositions and Methods for Treating Hair," filed Jun. 28, 2013.

Co-pending U.S. Appl. No. 13/931,222; Siliu Tan et al., "Compositions and Methods for Treating Hair," filed Jun. 28, 2013.

Co-pending U.S. Appl. No. 13/931,238; Siliu Tan et al., "Compositions and Methods for Treating Hair," filed Jun. 28, 2013.

Co-pending U.S. Appl. No. 13/931,248; Siliu Tan et al., "Compositions and Methods for Treating Hair," filed Jun. 28, 2013.

Co-pending U.S. Appl. No. 13/931,260; Siliu Tan et al., "Compositions and Methods for Treating Hair," filed Jun. 28, 2013.

Co-pending U.S. Appl. No. 13/931,276; Siliu Tan et al., "Compositions and Methods for Treating Hair," filed Jun. 28, 2013.

Co-pending U.S. Appl. No. 13/931,288; Siliu Tan et al., "Compositions and Methods for Treating Hair," filed Jun. 28, 2013.

Co-pending U.S. Appl. No. 13/931,298; Siliu Tan et al., "Compositions and Methods for Treating Hair," filed Jun. 28, 2013.

Co-pending U.S. Appl. No. 13/931,312; Siliu Tan et al., "Compositions and Methods for Treating Hair," filed Jun. 28, 2013.

International Search Report and Written Opinion for copending Application No. PCT/US2015/066818, dated Feb. 26, 2016.

Co-pending U.S. Appl. No. 14/576,639, Siliu Tan et al., "Hair Styling Compositions Comprising Latex Polymers," filed Dec. 19, 2014.

Co-pending U.S. Appl. No. 14/577,579, Siliu Tan et al., "Hair Styling Compositions Comprising Latex Polymers and Wax Dispersions," filed Dec. 19, 2014.

Co-pending U.S. Appl. No. 14/577,740, Christine Shin et al., "Hair Cosmetic Composition Containing Latex Polymers and a Silicone-Organic Polymer Compound," filed Dec. 19, 2014.

Co-pending U.S. Appl. No. 14/577,809, Mark Benn, "Hair Coloring Compositions Comprising Latex Polymers," filed Dec. 19, 2014.

(56) References Cited

OTHER PUBLICATIONS

Co-pending U.S. Appl. No. 14/578,074, Siliu Tan et al., "Compositions and Methods for Hair," filed Dec. 19, 2014.
Co-pending U.S. Appl. No. 14/578,122, Christine Shin, "Hair Cosmetic Composition Containing a Polyurethane Latex Polymer and a Silicone Organic Polymer Compound," filed Dec. 19, 2014.
Co-pending U.S. Appl. No. 14/586,105, Siliu Tan et al., "Compositions and Methods for Hair," filed Dec. 30, 2014.
International Search Report for Application No. PCT/US2014/044036, dated Oct. 21, 2014, 3 pages.
International Search Report for Application No. PCT/US2014/044377, dated Oct. 31, 2014, 3 pages.
International Search Report for Application No. PCT/US2014/044557, dated Oct. 13, 2014, 3 pages.
International Search Report for Application No. PCT/US2014/044587, dated Oct. 31, 2014, 3 pages.
International Search Report for Application No. PCT/US2014/044610, dated Oct. 31, 2014, 4 pages.
Polyquats As Conditioning Agents, 2009. Retrieved from the Internet.
English language abstract for DE 102009054516A1 (Jun. 16, 2011).
English language abstract for DE 2364398A1 (Oct. 30, 1975).
English language abstract for EP 0770375A1 (May 2, 1997).
English language abstract for EP 0847752A1 (Jun. 17, 1998).
English language abstract for EP 0898960A1 (Mar. 3, 1999).
English language abstract for EP 1082953A1 (Mar. 14, 2001).
English language abstract for FR 2633940B3 (Jul. 12, 1991).
English language abstract for FR 2834458A1 (Jul. 11, 2003).
English language abstract for FR 2898050A1 (Sep. 7, 2007).
English language abstract for FR 2961103A1 (Dec. 16, 2011).
English language abstract for FR 2968978A1 (Jun. 22, 2012).
English language abstract for JP H021956A (Jan. 8, 1990).
English language abstract for JP H05163124A (Jun. 29, 1993).
English language abstract for KR 20100105168A (Sep. 29, 2010).
International Search Report and Written Opinion for counterpart Application PCT/US2015/065967, dated Jul. 5, 2016.
International Search Report and Written Opinion for counterpart Application PCT/US2015/065975, dated Jul. 5, 2016.
Extended European Search Report for counterpart EP Application No. 14817057.4, dated Nov. 2, 2016.
Extended European Search Report for counterpart EP Application No. 14818467.4, dated Nov. 9, 2016.
Extended European Search Report for counterpart EP Application No. 14818460.9, dated Nov. 21, 2016.
Extended European Search Report for counterpart EP Application No. 14817786.8, dated Oct. 14, 2016.

\* cited by examiner

COMPOSITIONS AND METHODS FOR TREATING HAIR

TECHNICAL FIELD

The disclosure relates to hair styling compositions comprising at least two latex polymers, wherein at least one latex polymer is a film-forming polymer, and at least one component chosen from thickening agents. In various embodiments of the disclosure, the at least two latex polymers are chosen to have certain properties. Compositions comprising the at least two latex polymers and at least one component chosen from thickening agents may, according to certain embodiments, form films that have surprising properties. Methods of styling the hair with such compositions are also disclosed.

BACKGROUND

Compositions for styling the hair are known, such as, for example, hair spray compositions, hair gels and mousses, hair volumizing compositions, hair smoothing creams, lotions, serums, oils, clays, etc. The goals of many hair styling compositions include to hold or fix the hair in a particular shape, to impart or increase volume of the hair, and/or to smooth the hair, e.g. to decrease or eliminate the appearance of frizz.

Drawbacks associated with current products for styling the hair include that the product is often stick or tacky and/or often produces a film that imparts a sticky or tacky feel, and styled hair that is stiff and/or "crunchy" (i.e. the film is hard and brittle resulting in a crunching feel or sound when the hair is touched), which is undesirable for most consumers.

Current products for styling the hair typically include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, its viscosity builds up rapidly. Translated to styling applications, as the solvent evaporates, the polymer solution becomes thicker on the hair surface, resulting in a sticky or tacky film. These products also tend to exhibit problems with product spreadability, hair manageability, and low degree of humidity resistance which is particularly a problem in hot and humid countries.

The use of latex polymers is also known, for example, to provide extended-wear properties to a cosmetic product (e.g. mascara, eyeliner, nail polish) into which they are formulated.

Some known compositions include one latex polymer. For example, U.S. Pat. No. 6,126,929 describes a composition comprising a dispersion of a latex film former, optionally with a plasticizer, and a non film-forming particle not capable of being film-formed. U.S. Pat. No. 4,710,374 describes a composition comprising cationic polymers, a surfactant, and an anionic latex. U.S. Pat. No. 7,740,832 describes a composition comprising at least one non-latex polymer and an anionic, cationic or amphoteric fixing polymer. U.S. Pat. No. 4,798,721 describes a composition comprising a latex particle. U.S. Patent Application No. 2005/0089490 A1 describes a composition comprising a water-dispersible styling polymer and a gel-forming polymer.

Other known cosmetic compositions include various components to provide improved properties such as adhesion, flexibility, and compatibility of other components. For example, U.S. Patent Application No. 2007/0224140 A1 describes a composition comprising a cosmetically acceptable medium, a non film-forming microsphere to provide adhesion, and a film-forming component comprising two water-borne emulsion polymers. French Patent Application No. FR 2 968 978A describes an eyeliner composition comprising at least two film-forming latexes and a plasticizer to increase the flexibility of the film. French Patent Application No. FR 2 898 050A describes a composition comprising a fatty acid ester, and a copolymer of a (meth)acrylate polymer and a hydroxyester(meth)acrylate. U.S. Patent Application No. 2009/0297467A describes a composition comprising at least one neutralized sulfonated polymer and mixtures of acrylates and hydroxyester acrylates. U.S. Patent Application No. 2009/035335 A1 describes a mascara composition comprising two water-dispersible acrylate polymers, and a cross-linked polymeric film-former to enhance the compatibility and bind the two water-dispersible acrylate polymers. International Patent Application No. WO 2011/137338 A2 describes a composition comprising a polyurethane dispersion and an acrylic film-forming dispersion. U.S. Patent Application No. 2004/0071646A describes an aerosol device containing a composition comprising a polyurethane dispersion having a particle size of from 0.1-1 μm, and at least one non-latex fixing polymer.

Additionally, some cosmetic compositions incorporate polymers having a core-shell structure. For example, U.S. Patent Application No. 2003/0064045 A1 describes a mascara composition comprising a dispersion of particles having a core-shell structure. U.S. Patent Application No. 2007/0286833 A1 describes a multistage polymer comprising a latex core-shell particle comprising a soft polymer and a hard polymer. In addition, U.S. Patent Application No. 2009/0317432A describes an applicator for makeup containing a composition comprising a colorant and at least one latex or core-shell latex particle.

Cosmetic compositions in a non-aqueous medium are known. For example, European Patent Application No. EP 1 082 953A describes a dispersion comprising two film formers in isododecane. International Patent Application No. WO11056332A describes a composition comprising three volatile solvents, and at least one film former, for example silicon acrylate or acrylate, soluble or dispersible in at least one of the three solvents.

Compositions for use in mascaras may have low glass transition temperatures ("Tg") to obtain a soft film. For example, U.S. Patent Application No. 2010/0028284 A1 describes a mascara composition comprising at least two acrylate film formers, where the glass transition temperature ("Tg") of the mascara composition is ≤20° C. U.S. Patent Application No. 2006/134043A describes a mascara composition comprising a fatty acid and at least one acrylate resin emulsion.

Some known compositions use solubilized polymers rather than polymer particles. For example, U.S. Pat. No. 7,651,693 describes a composition comprising a solubilized blend of two polymers. U.S. Pat. No. 6,214,328 describes a composition comprising at least one acrylate latex that is soluble in solutions containing low volatile organic compounds or in water upon neutralization.

U.S. Pat. No. 5,441,728 describes a composition comprising a water-soluble fixative polymer and a latex particle. Water-soluble polymers tend to be sticky, and may not be suitable for applications requiring a clean touch.

French Patent Application No. FR 2 834 458A describes a nail polish composition comprising two film formers in an aqueous medium in a specific ratio.

However, it has now been discovered that by providing a composition comprising at least two latex polymers, wherein at least one of said latex polymers is a film-forming polymer, and at least one component chosen from thickening agents, it is possible to form a film on a substrate that has certain desirable properties, such as a clean, natural, and/or "invisible" feel, and a lack of stickiness. Such compositions may be useful in hair-styling applications wherein styling benefits such as a natural look, curling or straightening, and styling hold are imparted to hair.

Moreover, compositions according to embodiments of the disclosure may be prepared that deliver a surprisingly broad range of hair styling benefits, such as, for example, from low to high style-hold and curl-retention properties, for example by varying the weight ratio between both latex polymers, with or without additives.

DESCRIPTION OF EXEMPLARY EMBODIMENTS

The disclosure relates, in various embodiments, to compositions comprising at least two latex polymers, wherein at least one latex polymer is a film-forming polymer, and at least one component chosen from thickening agents. In various embodiments, the at least two latex polymers may be chosen to have certain properties. In at least certain embodiments, the at least two latex polymers are present in a combined amount ranging from about 0.1% to about 30% by weight, relative to the weight of the composition. In further embodiments, the at least two latex polymers are present in the composition in a weight ratio of about 10:1 to about 1:10.

The composition comprising the at least two polymers and at least one component chosen from thickening agents forms a film when applied to a substrate. In at least certain exemplary embodiments according to the disclosure, the resulting film formed by the composition comprising at least two latex polymers and at least one component chosen from thickening agents, is clear and/or transparent.

In further embodiments, methods of styling the hair are disclosed, said methods comprising applying compositions according to the disclosure to the hair. Such styling methods may comprise shaping, reshaping, positioning, repositioning, adding volume to, curling, or straightening the hair, in order to achieve a certain hair style or appearance.

Latex Polymers

According to various exemplary embodiments of the disclosure, the at least two latex polymers, at least one of which is a film-forming polymer, are chosen from acrylate and polyurethane polymers, with the proviso that when the first latex polymer is chosen from acrylate polymers, the second latex polymer is chosen from polyurethane polymers; and when the first latex polymer is chosen from polyurethane polymers, the second latex polymer is chosen from acrylate polymers.

In various embodiments according to the disclosure, the at least two latex polymers may be present in a combined amount ranging from about 0.1% to about 30% by weight, relative to the weight of the composition. In other embodiments, the at least two latex polymers may be present in the composition in a weight ratio of about 10:1 to about 1:10.

In various embodiments, the at least two latex polymers may be identified as polymer A and polymer B. Compositions according to certain embodiments may comprise at least one polymer A and at least one polymer B, wherein both polymer A and polymer B are film-forming polymers. In additional embodiments, the at least two latex polymers may be chosen from polymers A, B, and C, wherein polymers A and B are film-forming polymers and polymer C is not a film-forming polymer. At least one of the latex polymers is chosen to be a film-forming polymer, for instance, various combinations of A and A; B and B; A and B; A and C; B and C; and A, B, and C, and the like may be used.

In various embodiments, polymer A may be chosen from latex polymers having a Young's modulus ranging from about 0.1 MPa to about 10 MPa and a strain, under stress at 0.5 MPa, of at least about 1%; and polymer B may be chosen from latex polymers having a Young's modulus ranging from about 10 MPa to about 6 GPa and a strain, under stress at 0.5 MPa, of less than about 5%. In at least certain embodiments, polymer A may have a glass transition temperature (Tg) ranging from about −90° C. to about 40° C., and polymer B may have a glass transition temperature (Tg) ranging from about 40° C. to about 200° C. In at least certain other embodiments, the weight ratio of polymer A to polymer B in the compositions of the disclosure is from about 1:10 to about 1:1, from about 3:1 to about 10:1, or from about 5:1 to about 10:1. Polymers A and B may be chosen from acrylate and polyurethane polymers, with the proviso that when polymer A is chosen from an acrylate polymer, polymer B is chosen from a polyurethane polymer; and when polymer A is chosen from a polyurethane polymer, polymer B is chosen from an acrylate polymer.

In at least certain exemplary and non-limiting embodiments, latex polymers A and B may be chosen such that polymer A comprises at least one latex polymer that is a relatively soft, flexible latex polymer, and polymer B comprises at least one latex polymer that is a relatively hard, brittle polymer, although such characteristics are not required.

As used herein, a film-forming polymer is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at ambient temperature or below, or in other words, will only form a film at temperatures above ambient. For purposes of this disclosure, ambient temperature is taken as being below 40° C. such as in the range of 15° C. to 30° C.

By "at least two latex polymers," it is contemplated that more than two latex polymers may be chosen. Thus, for example, in various embodiments, the composition may comprise polymers A and/or B, which are latex film-forming polymers, and the composition may also comprise at least one latex polymer C that is a non-film-forming polymer; and so on.

According to certain embodiments, the compositions comprises exactly two latex polymers, at least one of which is a film-forming polymer. In further embodiments, the composition comprises exactly two latex polymers, both of which are film-forming polymers. In yet further embodiments, the composition comprises at least two latex polymers, both of which are film-forming polymers, but does not comprise any additional film-forming polymers.

In at least certain embodiments of the disclosure, the at least two latex polymers are provided in the form of aqueous dispersions prior to formulating the compositions of the disclosure. In various embodiments, the aqueous dispersions may be obtained through an emulsion polymerization of monomers wherein the resulting latex polymers have a particle size lower than about 1 µm. In at least one exemplary embodiment, a dispersion prepared by the polymerization in water of one or more monomers having a polymerizable double bond may be chosen. In another exemplary embodiment, the aqueous dispersions obtained through an emulsion polymerization may be spray-dried.

In other embodiments, the latex polymers are produced from condensation reactions between monomers and subsequently dispersed in an aqueous medium.

Thus, the latex polymers may, in various exemplary embodiments, exist as dispersed polymer particles in a dispersion medium, such as an aqueous dispersion medium. The latex polymers may, in certain embodiments, each be dispersed in independent dispersion media. In yet further embodiments, the latex polymers may be dispersed together in the same dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

In at least one embodiment, the solvent of the dispersion medium consists of water. In other embodiments, the solvent of the dispersion medium consists of water and at least one cosmetically acceptable organic solvent. In further embodiments, the solvent comprises water. In yet further embodiments, the solvent of the dispersion medium primarily comprises water. For example, the solvent of the dispersion medium may, in at least certain exemplary embodiments, comprise greater than 50% water, such as greater than 55% water, greater than 60% water, greater than 65% water, greater than 70% water, greater than 75% water, greater than 80% water, greater than 85% water, greater than 90% water, greater than 95% water, greater than 96% water, greater than 97% water, greater than 98% water, or greater than 99% water.

In embodiments according to the disclosure, the latex polymer particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In at least certain exemplary embodiments, latex particles according to the disclosure may have an average diameter ranging up to about 1000 nm, such as from about 50 nm to about 800 nm, or from about 100 nm to about 500 nm. Such particle sizes may be measured with a laser granulometer (e.g. Brookhaven BI90).

In various embodiments, the latex polymers may, independently, be neutralized, partially neutralized, or unneutralized. In exemplary embodiments where the latex polymers are neutralized or partially neutralized, the particle size may be, for example, greater than about 800 nm. In at least certain embodiments, the particulate form of the latex polymers is retained in the dispersion medium.

In further embodiments, the latex polymers may be chosen from uncharged and charged latex polymers. Thus, the latex polymers may, according to various exemplary embodiments, be chosen from nonionic latex polymers, cationic latex polymers, and anionic latex polymers.

As non-limiting examples of latex polymers that may be used, mention may be made, independently, of acrylate latex polymers and polyurethane latex polymers. As described herein, it is to be understood that when the first latex polymer is chosen from an acrylate polymer, the second latex polymer is chosen from a polyurethane polymer; and when the first latex polymer is chosen from a polyurethane polymer, the second latex polymer is chosen from an acrylate polymer.

By way of non-limiting example only, one of the at least two latex polymers may be chosen from acrylate latex polymers, such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl.

The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl(meth)acrylic, such as, for example, methyl(meth)acrylic, ethyl(meth) acrylic, propyl(meth)acrylic, isopropyl(meth)acrylic, butyl (meth)acrylic, tert-butyl(meth)acrylic, pentyl(meth)acrylic, isopentyl(meth)acrylic, neopentyl(meth)acrylic, hexyl (meth)acrylic, isohexyl(meth)acrylic, 2-ethylhexyl(meth) acrylic, cyclohexyl(meth)acrylic, isohexyl(meth)acrylic, heptyl(meth)acrylic, isoheptyl(meth)acrylic, octyl(meth) acrylic, isooctyl(meth)acrylic, as well as combinations of any of the above.

The esters of (meth)acrylic monomers may be, by way of non-limiting example, C1-C8 alkyl(meth)acrylates such as methyl(meth)acrylate, ethyl(meth)acrylate, propyl(meth) acrylate, isopropyl(meth)acrylate, butyl(meth)acrylate, tert-butyl(meth)acrylate, pentyl(meth)acrylate, isopentyl(meth) acrylate, neopentyl(meth)acrylate, hexyl(meth)acrylate, isohexyl(meth)acrylate, 2-ethylhexyl(meth)acrylate, cyclohexyl(meth)acrylate, isohexyl(meth)acrylate, heptyl(meth) acrylate, isoheptyl(meth)acrylate, octyl(meth)acrylate, isooctyl(meth)acrylate, allyl(meth)acrylate, and combinations thereof. Additional and non-limiting examples include C1-C8 alkoxy(meth)acrylates, such as methoxy(meth)acrylate, ethoxy(meth)acrylate, propyl oxide(meth)acrylate, isopropyl oxide(meth)acrylate, butyl oxide(meth)acrylate, tert-butyl oxide(meth)acrylate, pentyl oxide(meth)acrylate, isopentyl oxide(meth)acrylate, neopentyl oxide(meth)acrylate. The esters may be, by way of non-limiting example, C2-C6 hydroxy alkyl(meth)acrylates, such as hydroxy ethyl (meth)acrylate, 2-hydroxypropyl(meth)acrylate, glycidyl (meth)acrylate, ethylene glycol di(meth)acrylate, polyethylene glycol mono(meth)acrylate, 1,4-butane diol di(meth) acrylate, 1,6,hexane diol di(meth)acrylate, and any combination thereof. The esters may be, by way of non-limiting example, aryl(meth)acrylates such as benzyl(meth) acrylate, phenyl(meth)acrylate, and any combination thereof. The esters can further contain amino groups such as aminoethyl(meth)acrylate, N,N-dimethylaminoethyl(meth) acrylate, N,N-dimethylaminopropyl(meth)acrylate, N,N-dimethylaminodimethylpropyl(meth)acrylate, N,N-diethylaminoethyl(meth)acrylate, and N,N,N-trimethylaminoethyl (meth)acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N—(C1-C12)alkyl(meth)acrylates such as N-ethyl(meth)acrylamide, N-t-butyl(meth)acrylamide, N-t-octyl(meth)acrylamide, N-methylol(meth)acrylamide and N-diacetone(meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate, and combination thereof. Other non-limiting ionic monomers can include para-styrenesulfonic, vinylsulfonic, 2-(meth)acryloyloxyethylsulfonic, 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

Silicone acrylic polymers may also optionally be used as vinyl polymer in at least one exemplary and non-limiting embodiment.

In at least certain, non-limiting exemplary embodiments, acrylic latex polymers may be chosen from aqueous dispersions of Methacrylic Acid/Ethyl Acrylate copolymer (INCI: Acrylates Copolymer, such as LUVIFLEX® SOFT by BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI: Polyacrylate-2 Crosspolymer, such as FIXATE SUPERHOLD™ by Lubrizol), Styrene/Acrylic copolymer (such as NEOCRYL® A-1120, DSM), Ethylhexyl Acrylate/Methyl Methacrylate/Butyl Acrylate/Acrylic Acid/Methacrylic Acid copolymer (INCI: Acrylates/Ethylhexyl Acrylate Copolymer, such as DAITOSOL 5000SJ, Daito Kasei Kogyo), Acrylic/Acrylates Copolymer (INCI name: Acrylates Copolymer, such as DAITOSOL 5000AD, Daito Kasei Kogyo), and Acrylic Copolymers and Acrylates Copolymers, such as those known under the tradenames VINYSOL 2140 (Daido Chemical), ACULYN™ 33 (Dow Chemical), LUVIMER® MAE (BASF), or BALANCE CR (AKZO NOBEL).

In yet further exemplary and non-limiting embodiments, one of the at least two latex polymers may be chosen from polyurethane latex polymers, such as aqueous polyurethane dispersions comprising the reaction products of (i), (ii), and/or (iii), defined below.

Reaction product (i) may be any prepolymer according to the formula:

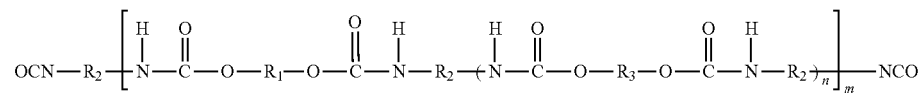

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecanedioic, 1,3-cyclohexanedicarboxylic, 1,4-cyclohexanedicarboxylic, 2,5-norbornanedicarboxylic, diglycolic, thiodipropionic, 2,5-naphthalenedicarboxylic, 2,6-naphthalenedicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythioether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexanediol. Polyacetals useful according to various non-limiting embodiments of the disclosure can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula $R_2(NCO)_2$, in which $R_2$ represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanatomethyl-3,5,5-trimethylcyclohexane (isophorone diisocyanate or IPDI), bis(4-isocyanatocyclohexyl)-methane, 1,3-bis(isocyanatomethyl)cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxycyclohexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylol-butanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

wherein R4 is chosen from alkylene or alkylene oxide radicals, said radicals not being substituted with ionic or potentially ionic groups.

Reaction product (ii) may optionally be chosen from alkylene diamines, such as hydrazine, ethylenediamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophoronediamine, and 4,4- methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

wherein R5 is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, R5 represents an alkylene radical substituted with sulphonic acid or sulphonate groups. By way of example only, the compound is chosen from sodium salts of N-(2-aminoethyl)-2-aminoethanesulphonic acid.

By way of non-limiting example, such latexes include, but are not limited to, aqueous polyurethane dispersions comprising a reaction product of a prepolymer comprising a dihydroxyl compound, a polyisocyanate, and a low molecular weight diol and at least two diamine compounds and wherein the composition is substantially free of triethanolamine stearate such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as Luviset® P.U.R, BASF), aliphatic polyurethane and aliphatic polyester polyurethane (such as the Neorez® series, DSM, such as Neorez® R989, INCI name: Polycarbamyl Polyglycol Ester).

In at least certain embodiments, the at least two latex polymers may be chosen from polyacrylic latex, polyacrylate latex, polystyrene latex, polyester latex, polyamide latex, polyurea latex, polyurethane latex, epoxy resin latex, cellulose acrylate latex, and their copolymers.

In various embodiments according to the disclosure, it may be possible to choose a polymer that comprises both acrylate and polyurethane parts at the molecular level.

Thickening Agents/Rheology Modifiers

The compositions according to various embodiments of the disclosure comprise at least one component chosen from thickening agents, also referred to interchangeably herein as thickeners or rheology modifiers. Thickening agents are generally used to modify the viscosity or rheology of compositions. However, without wishing to be bound by theory, it is believed that the presence of thickening agents in compositions according to the disclosure may lower the glass transition temperature, Tg, decrease the Young's modulus, and increase the strain of latex polymers and/or the films formed by latex polymers. In addition, without wishing to be bound by theory, it is believed that the addition of the at least one thickening agent may aid in the distribution of the composition on hair, may ease handling and/or manageability of the composition. Thus, while thickening agents may decrease the Tg of the film formed by the composition, thereby softening the film or coating formed by the latex polymers, it was surprisingly and unexpectedly found that the coating or film produced on hair treated with the compositions of the disclosure imparts a strong styling hold to the hair while leaving the hair with a natural/clean feel and look. As such, the flexibility and stiffness of the resulting film or coating may be more balanced and thus impart a better style and stronger hold to hair. It is also possible to render the hair softer, and/or generally improve the performance of the composition on the hair.

Non-limiting examples of thickening agents that may be used according to various embodiments of the disclosure include those conventionally used in cosmetics, such as polymers of natural origin and synthetic polymers. For example, nonionic, anionic, cationic, amphiphilic, and amphoteric polymers, and other known rheology modifiers, such as cellulose-based thickeners, may be chosen.

The thickening agents may be chosen from, for example, hydrophilic thickeners, for example cellulose polymers and gums. As used herein, the term "hydrophilic thickener" is meant to indicate that the thickening agent is soluble or dispersible in water. Non-limiting examples of hydrophilic thickeners include modified or unmodified carboxyvinyl polymers, such as the products sold under the name CARBOPOL (CTFA name: carbomer) by Goodrich, homopolymers or copolymers of acrylic or methacrylic acids or the salts thereof and the esters thereof, such as the products sold under the names VERSICOL F® or VERSICOL K® by Allied Colloid, ULTRAHOLD 8® by Ciba-Geigy, polyacrylates and polymethacrylates such as the products sold under the names LUBRAJEL and NORGEL by Guardian, or under the name HISPAJEL by Hispano Chimica, and polyacrylic acids of SYNTHALEN K type, polyacrylamides, copolymers of acrylic acid and of acrylamide sold in the form of the sodium salt thereof, such as under the names RETEN® by Hercules, the sodium polymethacrylate such as sold under the name DARVAN 7® by Vanderbilt, and the sodium salts of polyhydroxycarboxylic acids such as sold under the name HYDAGEN F® by Henkel, optionally crosslinked and/or neutralized 2-acrylamido-2-methylpropanesulphonic acid polymers and copolymers, for instance poly(2-acrylamido-2-methylpropanesulphonic acid) such as sold by Clariant under the name HOSTACERIN AMPS (CTFA name: ammonium polyacryldimethyltauramide), crosslinked anionic copolymers of acrylamide and of AMPS, e.g. in the form of a water-in-oil emulsion, such as those sold under the name SEPIGEL™ 305 (CTFA name: Polyacrylamide/C13-14 Isoparaffin/Laureth-7) and under the name SIMULGEL™ 600 (CTFA name: Acrylamide/Sodium acryloyldimethyltaurate copolymer/Isohexadecane/Polysorbate 80) by SEPPIC, polyacrylic acid/alkyl acrylate copolymers of PEMULEN type, associative polymers, for instance PEG-150/stearyl alcohol/SMDI copolymer such as sold under the name ACULYN™ 46 by Rohm & Haas, steareth-100/PEG-136/HDI copolymer such as sold under the name RHEO-LATE FX 1100 by Elementis), as well as mixtures thereof.

Other exemplary hydrophilic thickeners include associative polymers. As used herein, the term "associative polymer" is intended to mean any amphiphilic polymer comprising in its structure at least one fatty chain and at least one hydrophilic portion. The associative polymers in accordance various exemplary embodiments may be anionic, cationic, nonionic or amphoteric. By way of example, associative polymers which may be chosen include those comprising at least one hydrophilic unit and at least one fatty-chain allyl ether unit, such as those in which the hydrophilic unit is constituted of an ethylenic unsaturated anionic monomer, such as a vinylcarboxylic acid or an acrylic acid, a methacrylic acid, and mixtures thereof, and in which the fatty-chain allyl ether unit corresponds to the monomer of formula (I) below:

$$CH_2=C(R')CH_2OB_nR \qquad (I)$$

in which R' is chosen from H or $CH_3$, B is chosen from an ethyleneoxy radical, n is zero or is chosen from an integer ranging from 1 to 100, and R is chosen from a hydrocarbon-based radical chosen from alkyl, arylalkyl, aryl, alkylaryl and cycloalkyl radicals containing from 8 to 30 carbon atoms, such as from 10 to 24 carbon atoms, or from 12 to 18 carbon atoms. Exemplary and non-limiting polymers of this type are described and prepared, according to an emulsion polymerization process, in patent EP 0 216 479.

Non-limiting examples of associative anionic polymers that may also be chosen include anionic polymers comprising at least one hydrophilic unit of olefinic unsaturated carboxylic acid type, and at least one hydrophobic unit exclusively of $(C_{10}\text{-}C_{30})$alkyl ester of unsaturated carboxylic acid type. Examples that may be mentioned include, but are not limited to, the anionic polymers described and prepared according to U.S. Pat. Nos. 3,915,921 and 4,509,949.

Cationic associative polymers that may be chosen include, but are not limited to, quaternized cellulose derivatives and polyacrylates containing amine side groups.

Exemplary non-ionic associative polymers include celluloses modified with groups comprising at least one fatty chain, for instance hydroxyethyl celluloses modified with groups comprising at least one fatty chain, such as alkyl groups, e.g. $C_8\text{-}C_{22}$ alkyl groups, arylalkyl and alkylaryl groups, such as cetyl hydroxyethyl cellulose, also known as Natrosol® Plus (sold by the company Ashland); Bermocoll EHM 100 (sold by the company Berol Nobel), Amercell Polymer HM-1500® sold by Amerchol (hydroxyethylcellulose modified with a polyethylene glycol (15) nonylphenyl ether group, sold by the company Amerchol), celluloses modified with polyalkylene glycol alkylphenyl ether groups, guars such as hydroxypropyl guar, optionally modified with groups comprising at least one fatty chain such as an alkyl chain, for example JAGUAR® XC-95/3 (C14 alkyl chain, sold by the company Rhodia Chimie); Esaflor HM 22 (C22 alkyl chain, sold by the company Lamberti); RE210-18 (C14 alkyl chain) and RE205-1 (C20 alkyl chain, sold by the company Rhodia Chimie), copolymers of vinylpyrrolidone and of fatty-chain hydrophobic monomers, for instance Antaron® or Ganex® V216 (vinylpyrrolidone/hexadecene copolymers); Antaron® or Ganex® V220 (vinylpyrrolidone/ eicosene copolymers), sold by the company I.S.P., copolymers of $C_1\text{-}C_6$ alkyl methacrylates or acrylates and of amphiphilic monomers comprising at least one fatty chain, and copolymers of hydrophilic methacrylates or acrylates and of hydrophobic monomers comprising at least one fatty chain, for instance the polyethylene glycol methacrylate/lauryl methacrylate copolymer.

Associative polyurethanes may also be chosen in various exemplary and non-limiting embodiments. These are nonionic block copolymers comprising in the chain both hydrophilic blocks usually of polyoxyethylene nature, and hydrophobic blocks that may be aliphatic sequences alone and/or cycloaliphatic and/or aromatic sequences. Associative polyurethanes comprise at least two hydrocarbon-based lipophilic chains containing from $C_6$ to $C_{30}$ carbon atoms, separated by a hydrophilic block, the hydrocarbon-based chains optionally being pendent chains or chains at the end of a hydrophilic block. For example, it is possible for one or more pendent chains to be provided. In addition, the polymer may comprise a hydrocarbon-based chain at one or both ends of a hydrophilic block. The associative polyurethanes may be arranged in triblock or multiblock form. The hydrophobic blocks may thus be at the each end of the chain (for example, triblock copolymer with a hydrophilic central block) or distributed both at the ends and within the chain (for example, multiblock copolymer). These polymers may also be graft polymers or starburst polymers. For example, the associative polyurethanes may be triblock copolymers in which the hydrophilic block is a polyoxyethylene chain containing from 50 to 1000 oxyethylene groups.

By way of non-limiting example, associative polymers of the polyurethane polyether type that may be used include the polymer $C_{16}\text{-}OE_{120}\text{-}C_{16}$ from Servo Delden (under the name SER AD FX1100), which is a molecule containing a urethane function and having a weight-average molecular weight of 1300), OE being an oxyethylene unit, Nuvis® FX 1100 (European and US INCI name "Steareth-100/PEG-136/HMDI Copolymer" sold by the company Elementis Specialties), and also Acrysol RM 184® (sold by the company Rohm and Haas); Elfacos T210® (C12-C14 alkyl chain) and Elfacos T212® (C18 alkyl chain) sold by the company Akzo. Further exemplary associative polymers that may be chosen include RHEOLATE® 205 containing a urea function, sold by Rheox, or RHEOLATE® 208 or 204, or RHEOLATE® FX1100 from Elementis. The product DW 1206B from Rohm & Haas containing a $C_{20}$ alkyl chain with a urethane bond, sold at a solids content of 20% in water, may also be used.

In yet further exemplary embodiments, solutions or dispersions of these polymers, especially in water or in aqueous-alcoholic medium, may be chosen. Examples of such polymers include SER AD FX1010, SER AD FX1035 and SER AD 1070 from Servo Delden, and RHEOLATE® 255, RHEOLATE® 278 and RHEOLATE® 244 sold by Rheox. Further examples include the products ACULYN™ 46, DW 1206F and DW 1206J, and also ACRYSOL RM 184 or ACRYSOL 44 from Rohm & Haas, and BORCHIGEL LW 44 from Borchers.

In at least one exemplary embodiment, the at least one thickening agent is chosen from copolymers resulting from the polymerization of at least one monomer (a) chosen from carboxylic acids possessing α,β-ethylenically unsaturated groups or their esters, with at least one monomer (b) possessing ethylenically unsaturated groups and comprising a hydrophobic group. Such copolymers may exhibit emulsifying properties.

As used herein, the term "copolymers" is intended to mean both copolymers obtained from two types of monomers and those obtained from more than two types of monomers, such as, for example, terpolymers obtained from three types of monomers. The chemical structure of the copolymers comprises at least one hydrophilic unit and at least one hydrophobic unit. The expression "hydrophobic unit" or "hydrophobic unit" is understood to mean a radical possessing a saturated or unsaturated and linear or branched hydrocarbon-based chain which comprises at least 8 carbon atoms, for example from 10 to 30 carbon atoms, as a further example from 12 to 30 carbon atoms, and as yet a further example from 18 to 30 carbon atoms.

In certain exemplary and non-limiting embodiments, the thickening copolymers are chosen from the copolymers resulting from the polymerization of:

(1) at least one monomer of formula (II):

$$CH_2=CH(R_1)COOH \quad (II)$$

wherein $R_1$ is chosen from H or $CH_3$ or $C_2H_5$, providing acrylic acid, methacrylic acid, or ethacrylic acid monomers, and (2) at least one monomer of $(C_{10}$-$C_{30})$alkyl ester of unsaturated carboxylic acid type corresponding to the monomer of formula (III):

$$CH_2=CH(R_2)COOR_3 \quad (III)$$

wherein $R_2$ is chosen from H or $CH_3$ or $C_2H_5$, providing acrylate, methacrylate or ethacrylate units, $R_3$ denoting a $C_{10}$-$C_{30}$ alkyl radical, such as a $C_{12}$-$C_{22}$ alkyl radical.

Non-limiting examples of $(C_{10}$-$C_{30})$alkyl esters of unsaturated carboxylic acids are for example chosen from lauryl acrylate, stearyl acrylate, decyl acrylate, isodecyl acrylate, dodecyl acrylate and the corresponding methacrylates, such as lauryl methacrylate, stearyl methacrylate, decyl methacrylate, isodecyl methacrylate and dodecyl methacrylate, and mixtures thereof.

Additionally, crosslinked thickening polymers may be chosen according to further exemplary embodiments. For example, such polymers may be chosen from polymers resulting from the polymerization of a mixture of monomers comprising:

(1) acrylic acid,
(2) an ester of formula (III) described above, in which $R_2$ is chosen from H or $CH_3$, $R_3$ denoting an alkyl radical having from 12 to 22 carbon atoms, and
(3) a crosslinking agent, which is a well-known copolymerizable polyethylenic unsaturated monomer, such as diallyl phthalate, allyl(meth)acrylate, divinylbenzene, (poly)ethylene glycol dimethacrylate and methylenebisacrylamide.

By way of example, crosslinked thickening polymers comprising about 60% to about 95% by weight of acrylic acid (hydrophilic unit), about 4% to about 40% by weight of $C_{10}$-$C_{30}$ alkyl acrylate (hydrophobic unit), and about 0% to about 6% by weight of crosslinking polymerizable monomer. In yet further embodiments, the crosslinked thickening polymers may comprise about 96% to about 98% by weight of acrylic acid (hydrophilic unit), about 1% to about 4% by weight of $C_{10}$-$C_{30}$ alkyl acrylate (hydrophobic unit), and about 0.1% to 0.6% by weight of crosslinking polymerizable monomer, such as those described above.

For example, acrylate/$C_{10}$-$C_{30}$ alkyl acrylate copolymers (INCI name: Acrylates/C10-30 Alkyl Acrylate Crosspolymer), such as the products sold by Lubrizol under the trade names PEMULEN™ TR1, PEMULEN™ TR2, CARBOPOL® 1382 and CARBOPOL® EDT 2020 may be chosen.

In further embodiments, the at least one thickening agent may be chosen from nonionic homopolymers or copolymers containing ethylenically unsaturated monomers of the ester and/or amide type. For example, the products sold under the names CYANAMER P250 by the company CYTEC (polyacrylamide), methyl methacrylate/ethylene glycol dimethacrylate copolymers (such as PMMA MBX-8C by the company US COSMETICS), butyl methacrylate/methyl methacrylate copolymers (such as ACRYLOID B66 by the company RHOM HMS), and polymethyl methacrylates (BPA 500 by the company KOBO) may be chosen.

In yet further embodiments, the at least one thickening agent chosen from polymers of natural origin may include, for example, thickening polymers comprising at least one sugar unit, for instance nonionic guar gums, optionally modified with C1-C6 hydroxyalkyl groups; biopolysaccharide gums of microbial origin, such as scleroglucan gum (also known as sclerotium gum) or xanthan gum; gums derived from plant exudates, such as gum arabic, ghatti gum, karaya gum, gum tragacanth, carrageenan gum, agar gum and carob gum, ceratonia siliqua gum and *cyamopsis tetragonoloba* (guar) gum; pectins; alginates; starches; hydroxy(C1-C6)alkylcelluloses and carboxy(C1-C6)alkylcelluloses.

Non-limiting examples of nonionic, unmodified guar gums that may be used in various embodiments include Guargel D/15 (Noveon); Vidogum GH 175 (Unipectine), Meypro-Guar 50 and JAGUAR® C (Meyhall/Rhodia Chimie). Non-limiting examples of nonionic modified guar gums include JAGUAR® HP8, HP60, HP120, DC 293 and HP 105 (Meyhall/Rhodia Chimie); and Galactasol 4H4FD2 (Ashland).

Further examples of useful thickening agents include scleroglucans, for example, Actigum™ CS from Sanofi Bio Industries; Amigel from Alban Muller International, and also the glyoxal-treated scleroglucans described in FR2633940); xanthan gums, for instance Keltrol®, Keltrol® T, Keltrol® Tf, Keltrol® Bt, Keltrol® Rd, Keltrol® Cg (Nutrasweet Kelco), Rhodicare® S and Rhodicare® H (Rhodia Chimie); starch derivatives, for instance Primogel® (Avebe); hydroxyethylcelluloses such as Cellosize® QP3L, QP4400H, QP30000H, HEC30000A and Polymer PCG10 (Amerchol), Natrosol™ 250HHR®, 250MR, 250M, 250HHXR, 250HHX, 250HR, HX (Hercules) and Tylose® H1000 (Hoechst); hydroxypropylcelluloses, for instance Klucel® EF, H, LHF, MF and G (Ashland); carboxymethylcelluloses, for instance Blanose® 7M8/SF, refined 7M, 7LF, 7MF, 9M31F, 12M31XP, 12M31P, 9M31XF, 7H, 7M31, 7H3SXF (Ashland), Aquasorb® A500 (Hercules), Ambergum® 1221 (Hercules), Cellogen® HP810A, HP6HS9 (Montello) and Primellose® (Avebe).

Exemplary modified nonionic guar gums may, for example, be modified with C1-C6 hydroxyalkyl groups. Exemplary hydroxyalkyl groups may include hydroxymethyl, hydroxyethyl, hydroxypropyl and hydroxybutyl groups.

Guar gums are well known in the state of the art and may, for example, be prepared by reacting the corresponding alkene oxides, such as for example propylene oxides, with guar gum so as to obtain a guar gum modified with hydroxypropyl groups. The hydroxyalkylation ratio, which corresponds to the number of alkylene oxide molecules consumed to the number of free hydroxyl functional groups present on the guar gum, may in at least certain exemplary embodiments vary from about 0.4 to about 1.2.

Exemplary and non-limiting nonionic guar gums, optionally modified with hydroxyalkyl groups, include those sold under the trade names JAGUAR® HP8, JAGUAR® HP60 and JAGUAR® HP120, JAGUAR® DC 293 and JAGUAR® HP 105 by the company RHODIA CHIMIE (RHODIA CHIMIE), and under the name GALACTASOL™ 4H₄FD2 by the company ASHLAND.

Guar gums may also be modified with a quaternary ammonium group. Guar gums modified as such include Guar Hydroxypropyltrimonium Chloride, also known under the tradename JAGUAR® C-13S(RHODIA CHIMIE).

Exemplary and non-limiting celluloses include hydroxyethylcelluloses and hydroxypropylcelluloses. The products sold under the names KLUCEL EF, KLUCEL H, KLUCEL LHF, KLUCEL MF, KLUCEL G, by the company ASHLAND, CELLOSIZE POLYMER PCG-10 by the company AMERCHOL, may be chosen in various embodiments.

Exemplary, non-limiting thickening polysaccharides may be chosen from glucans, modified or unmodified starches (such as those derived, for example, from cereals such as wheat, corn or rice, vegetables such as golden pea, tubers such as potato or cassava), amylose, amylopectin, glycogen, dextrans, celluloses and derivatives thereof (methylcelluloses, hydroxyalkylcelluloses, ethylhydroxyethylcelluloses), mannans, xylans, lignins, arabans, galactans, galacturonans, chitin, chitosans, glucoronoxylans, arabinoxylans, xyloglucans, glucomannans, pectic acids and pectins, arabinogalactans, carrageenans, agars, gums arabic, gums tragacanth, Ghatti gums, Karaya gums, carob gums, galactomannans such as guar gums and their nonionic derivatives (hydroxypropylguar), and mixtures thereof.

Further, exemplary thickening agents include silicas, optionally hydrophobic, such as those described in EP-A-898960, and for example marketed as AEROSIL® R812 by the company Degussa, CAB-O-SIL TS-530, CAB-O-SIL TS-610, CAB-O-SIL TS-720 by the company Cabot, AEROSIL® R972, AEROSIL® R974 by the company Degussa; clays, such as montmorillonite, modified clays such as the bentones for example, stearalkonium hectorite, stearalkonium bentonite; polysaccharide alkyl ethers (optionally with the alkyl group having from 1 to 24 carbon atoms, for example from 1 to 10 carbon atoms, as a further example from 1 to 6 carbon atoms, and as yet a further example from 1 to 3 carbon atoms) such as those described in document EP-A-898958.

Thickening agents of the present disclosure may also include rheology modifiers. In accordance with the disclosure, rheology modifiers may, in various exemplary embodiments, be chosen from Polyacrylamide(and)C13-14 Isoparaffin(and)Laureth-7 (Sepigel™ 305 from Seppic), Hydroxypropyl Guar (JAGUAR® HP105 from Rhodia), *Cyamopsis Tetragonoloba* (Guar) Gum (Supercol U Guar Gum from Ashland), Acrylates/C10-30 Alkyl Acrylate Crosspolymer (Carbopol® Ultrez 20 Polymer from Lubrizol), Acrylates/C10-30 Alkyl Acrylate Crosspolymer (Permulen™ TR-1 from Lubrizol), Polyacrylate Crosspolymer-6 (Sepimax Zen from Seppic), Sclerotium Gum (Amigum from Alban Muller), Xanthan Gum(and)Ceratonia Siliqua Gum (Nomcort CG from Nisshin Oil Lio), Hydroxypropyl Guar (Jaguar® HP8 from Rhodia), Guar Hydroxypropyl Trimonium Chloride (Jaguar® C-13-S from Rhodia), Hydroxyethyl Cellulose (Natrosol® 250 MR from Ashland).

When anionic thickening agents are used, they are generally neutralized before being included in or as they are added to the compositions of the disclosure. Such anionic thickening agents may be neutralized by employing traditional neutralizing agents such as alkanolamines, for example, monoethanolamine and diethanolamine; aminomethyl propanol; basic amino acids, for example arginine and lysine; and ammonium compounds and their salts. The anionic thickening agents may also be neutralized by at least one latex polyurethane polymer of the disclosure wherein said latex polyurethane polymer has at least one free amino group and/or is provided in a dispersion medium that has a pH of greater than 7.

Cationic thickening agents of the disclosure may also be chosen from non-associative cationic polymers such as dimethylaminoethyl methacrylate homopolymers quaternized with methyl chloride or dimethylaminoethyl methacrylate copolymers quaternized with methyl chloride and acrylamide. Among the homopolymers of this type, mention may be made of the products sold under the names Salcare SC95 and Salcare SC96 by the company Ciba and SYNTHALEN® CR by the company 3V Sigma (chemical name: methacryloylethyl trimethyl ammonium chloride homopolymer, INCI name: polyquaternium-37). Among the copolymers of this family, mention may be made of the product Salcare S C92 sold by Ciba or the product PAS 5 194 sold by Hoechst.

Another suitable example of a cationic thickening agent is a product known by the INCI name of polyacrylate-1 crosspolymer (Carbopol® Aqua CC, from the company, Lubrizol).

It is contemplated that, in at least certain exemplary and non-limiting embodiments, the thickening agents of the disclosure may include compounds such as gellifying and viscosity modifying agents. For example, compositions of the disclosure may employ at least one water-soluble resin such as polyethylene oxide having a molecular weight ranging from 100,000 to 10,000,000. Examples of such polyethylene oxides include, but not limited to, Polyox water-soluble resins manufactured by Dow under the INCI names of PEG-2M, PEG-5M, PEG-7M, PEG-14M, PEG-23M, PEG-45M, PEG-90M, PEG-160M, and PEG-180M. PEG-90M is known under the tradename of Polyox™ WSR 301, and PEG-45M is known under the tradename Polyox™ WSR 60k. The amounts of water-soluble resins in the compositions, when present, may range from about 0.1% to about 2% by weight relative to the total weight of the composition.

It is to be understood that any combination of the above mentioned agents is contemplated according to various exemplary embodiments of the disclosure.

Compositions

As described herein, exemplary compositions according to the disclosure may comprise at least two latex polymers chosen from acrylate and polyurethane polymers, with the proviso that when the first latex polymer is chosen from acrylate polymers, the second latex polymer is chosen from polyurethane polymers; and when the first latex polymer is chosen from polyurethane polymers, the second latex polymer is chosen from acrylate polymers. The compositions further comprise at least one component chosen from thickening agents.

In certain embodiments, each of the latex polymers is present in an amount ranging from about 0.05% to about 10% by weight, such as about 0.1% to about 7.5% by weight, such as about 0.25% to about 5% by weight, such as about 0.5% to about 2.5% by weight, or about 0.5% to about 1.5% by weight, relative to the weight of the composition, including all ranges and subranges there between. In other embodiments, each of the latex polymers is present in an amount ranging from about 1% to about 15% by weight, such as about 1% to about 12% by weight, such as about 1.2% to about 12% by weight, such as about 1.5% to about 10% by weight, or such as less than about 10% by weight, relative to the weight of the composition, including all ranges and subranges there between. In yet other embodiments, each of the latex polymers is present in an amount ranging from about 0.1% to about 2% by weight, such as about 0.15% to about 1.9% by weight, or such as about 0.18% to about 1.8% by weight, relative to the weight of the composition, including all ranges and subranges there between.

In certain embodiments, the latex polymers are present in a combined amount ranging from about 0.1% to about 30% by weight, such as about 0.1% to about 25% by weight, such as about 0.2% to about 20% by weight, such as about 0.2% to about 15% by weight, such as about 0.5% to about 10% by weight, such as about 1% to about 8% by weight, such as about 1% to about 5% by weight, such as about 1% to about 3% by weight, or such as below about 30% by weight, or such as about 25% by weight, or such as about 20% by weight, relative to the weight of the composition, including all ranges and subranges there between. By way of non-limiting example, the combined amount of latex polymers may be about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight, relative to the weight of the composition.

In yet further embodiments, the combined amount of latex polymers ranges up to about 30%, such as up to about 29%, such as up to about 28%, such as up to about 27%, such as up to about 26%, such as up to about 25%, such as up to about 24%, such as up to about 23%, such as up to about 22%, such as up to about 21%, such as up to about 20%, such as up to about 19%, up to about 18%, up to about 17%, up to about 16%, up to about 15%, up to about 14%, up to about 13%, up to about 12%, up to about 11%, up to about 10%, up to about 10%, up to about 9%, up to about 8%, up to about 7%, up to about 6%, up to about 5%, up to about 4%, up to about 3%, up to about 2%, or up to about 1%, each by weight, relative to the weight of the composition. In at least one exemplary embodiment, the combined amount of latex polymers is less than about 10% by weight, such as less than about 5% by weight, relative to the weight of the composition.

According to various embodiments of the disclosure, the weight ratio of the at least two latex polymers, e.g. polymer A to polymer B, may range from about 10:1 to about 1:10, such as about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2, including all ranges and subranges there between.

According to various embodiments of the disclosure, the weight ratio of polymer A to polymer B is about 10:1, about 9:1, about 8:1, about 7:1, about 6:1, about 5:1, 4:1, about 3:1, about 2:1, about 1:1, about 1:2, about 1:3, about 1:4, about 1:5, about 1:6, about 1:7, about 1:8, about 1:9, or about 1:10.

In at least certain exemplary and non-limiting embodiments, when polymer A is chosen from latex polymers having a Young's modulus ranging from about 0.1 MPa to about 10 MPa and a strain, under stress at 0.5 MPa, of at least about 1%, and polymer B is chosen from latex polymers having a Young's modulus ranging from about 10 MPa to about 6 GPa and a strain, under stress at 0.5 MPa, of less than about 5%, different weight ratios of polymer A to polymer B may be chosen to correspond to different hair styling applications. By way of example only, a weight ratio of polymer A to polymer B ranging from about 1:10 to about 1:1 may, in some embodiments, provide a high level of style hold; a weight ratio of polymer A to polymer B ranging from about 5:1 to about 10:1 may, in some embodiments, provide a medium to high level of style hold; and a weight ratio of polymer A to polymer B ranging from about 3:1 to about 10:1 may, in some embodiments, provide a light to medium level of style hold.

According to various embodiments, the at least one component chosen from thickening agents may be present in an amount ranging from about 0.1% to about 10% by weight, such as from about 0.1% to about 5% by weight, from about 0.5% to about 4% by weight, or from about 1% to about 3% by weight, based on the total weight of the composition.

In addition to the at least two latex polymers, wherein at least one is a film-forming polymer, and at least one component chosen from thickening agents, the compositions may further comprise at least one solvent. The at least one solvent may be chosen from water, at least one cosmetically acceptable organic solvent, or a mixture of water and at least one cosmetically acceptable organic solvent. Cosmetically acceptable organic solvents may, in various embodiments, be water-miscible, e.g. a mixture capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

The at least one solvent may be present in an amount ranging up to about 95%, such as from about 1% to about 90%, from about 5% to about 80%, or from about 10% to about 60% by weight, relative to the total weight of the composition.

In at least certain exemplary embodiments, the latex polymer particles are not soluble in the solvent of the composition, and thus remain in particulate form even after evaporation of the solvent. For example, in embodiments where the composition comprises alcohol as a cosmetically acceptable organic solvent, the latex particles may remain in particulate form upon evaporation of the alcohol, such as once the composition is applied to a substrate.

Compositions according to various embodiments of the disclosure may further comprise additional components that are typically used in hair styling compositions. Such components are known to those of skill in the art, or are within the ability of those of skill in the art to determine depending on the particular application, such as, for example, the particular component and/or amount thereof. Such components include, but are not limited to, coalescing agents and plasticizers.

In various embodiments, the compositions described herein may have a pH ranging from about 2 to about 9, such as about 3 to about 8, or about 4 to about 7.

In at least certain exemplary embodiments, the compositions are in the form of hair styling compositions, in any form, such as, for example, a gel, a cream, a foam, a lotion, an emulsion, or a liquid that may be sprayed onto or otherwise applied to the hair. In various embodiments, the composition may be provided in the form of a gel, a mousse, or a spray. In at least certain embodiments, the composition may be applied to the hair by first applying to the hands, and then contacting the hair with the hands; in other embodiments, the composition may be applied directly onto the hair, such as by spraying. The compositions may, in various embodiments, be applied to the hair as a leave-on treatment.

In various embodiments, the application of an external stimuli, such as heat, may be desirable as part of the hair styling process. By way of example only, before, during, or after the composition is applied to wet or dry hair, the hair may optionally be further treated with an external stimuli, for example with heat ranging from about 25° C. to about 250° C. In at least certain embodiments, the hair may also be shaped or positioned as desired while exposed to external stimuli, such as while heated or exposed to heat.

Professional and consumer heating tools can be used as a means to deliver heat or an elevated temperature to the hair. The heating tools can generate heat through electrical current or heating lamps. Depending upon the desired style, these tools include, but are not limited to, heaters, blow dryers, flat irons, hot combs, hot curler sets, steam pods, heated crimpers, heated lash curlers, heated wands/brushes, and hood driers or their combinations thereof.

As described, compositions according to the disclosure may impart a film on a substrate, such as on the hair or on the hand during or after application to the hair. A film formed by the composition may, surprisingly, be clean-feeling and not sticky, as with traditional hair styling compositions. Also surprisingly, the composition may impart a film on the hair that leaves the hair relatively natural and clean-feeling, yet has a flexible coating, leaving little to no residue, allows the hair to be bouncy and springy with little to no frizz or flaking, may impart relatively high definition with individualized curls, style control, volume, and shine, and/or may allow for relatively long-lasting hold and style memory. Furthermore, in at least certain embodiments according to the disclosure, the compositions are not sticky or tacky. A user of hair compositions according to various embodiments described herein may thus feel that the composition is not perceptible or is "invisible," yet still effectively style and/or hold the hair. Additionally, the compositions may have effective hair styling and/or hold properties, even in conditions of high, or relatively high, humidity. In at least certain embodiments according to the disclosure, the compositions may be quick-drying, which may allow drying and/or styling time to be reduced, as well as further improve ease of styling and curl retention.

Furthermore, as described, compositions prepared according to various embodiments may provide for varying degrees of hold to be imparted to a hair style. By way of non-limiting example only, in order to obtain a spiky look to hair of a very short length, a high level of styling hold may be desirable. Or, as a further non-limiting example, in order to obtain a flowing look or to maintain hair curls for hair of medium length or longer length, a light to medium level of style hold may be desirable. By altering the weight ratio of the first and second polymers, it is possible to formulate compositions having high levels of style hold, medium to high levels of style hold, medium levels of style hold, or light to medium levels of style hold.

In at least certain embodiments, a film formed by the compositions described herein may be clear and/or stable. In such embodiments, phase separation and dramatic aggregation are minimized.

In addition, hair styled or treated with compositions according to the disclosure may, in at least certain exemplary embodiments, be hydrophobic, and/or may appear less frizzy and/or may be less prone to breakage, relative to hair subjected to the same conditions but not having been styled or treated with a composition according to the disclosure.

It should be noted, however, that compositions and films, as well as hair to which the composition or film has been applied, according to the disclosure may not have one or more of the herein-referenced properties, yet are intended to be within the scope of the disclosure.

Also disclosed herein are methods for styling the hair, said methods comprising applying a composition according to the disclosure to the hair, either before, during, or after styling the hair. One or more steps of treating the hair with an external stimuli, such as heat, before, during, or after the composition has been applied to the hair are also contemplated.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a surfactant" is intended to mean at least one surfactant.

Unless otherwise indicated, all numbers used in the specification and claims are to be understood as being modified in all instances by the term "about," whether or not so stated. The term "about" as it modifies numbers herein is meant to indicate a difference of 10% or less from the stated number, such as 9% or less, such as 8% or less, such as 7% or less, such as 6% or less, such as 5% or less, such as 4% or less, such as 3% or less, such as 2% or less, or such as 1% or less, in various exemplary embodiments. Thus, by way of example only, in one embodiment where "about" indicates a difference of 10% or less, the phrase "about 20%" is intended to encompass a range from 18%-22%. In another exemplary embodiment where "about" indicates a difference of 5% or less, the phrase "about 20%" is intended to encompass a range from 19%-21%. All such numbers within each specified range are hereby explicitly intended to be included in the disclosure.

It should also be understood that the precise numerical values used in the specification and claims form additional embodiments of the disclosure, and are intended to include any ranges which can be narrowed to any two end points disclosed within the exemplary ranges and values provided, as well as the specific end points themselves. Efforts have been made to ensure the accuracy of the numerical values disclosed herein. Any measured numerical value, however, can inherently contain certain errors resulting from the standard deviation found in its respective measuring technique.

It should be understood that compositions according to various embodiments of the disclosure form a film when applied to a substrate. However, the various properties of the film described herein are intended to include any film provided by compositions according to the disclosure, regardless of whether the film is attached or bonded to the substrate or not. By way of example only, once the compositions are applied to a substrate and a film is formed, the film may subsequently be removed in order to evaluate properties such as strain and Young's modulus.

EXAMPLES

The following Examples are intended to be non-restrictive and explanatory only, with the scope of the invention being defined by the claims.

Procedures

A. Procedure for Determination of Physical Properties of Films

Film Plating:

The latex film was obtained by allowing a 30 gram water solution containing 4 grams of the latex polymer(s) to dry slowly in a 100 mL PFA Petri dish (100 mm diameter×15 mm height) at room temperature for at least 3 days.

Film Measurement:

The latex film, with known dimensions (length, width, thickness), was mounted on the Q800 Dynamic Mechanical Analysis from TA Instrument, and tested in a DMA Control Force mode. The stress/strain test was obtained using the following procedure:

Preload force: 0.001 N
Isothermal: 25° C.
Soak time: 0.5 minutes
Force ramp rate: 0.5N/min to 18 N The test ended when the sample broke, 18 N force was reached, or maximum displacement was achieved (25.5 mm).

From the stress/strain curve, the Young's Modulus was calculated as the slope of the linear portion at about 0.01% Strain to about 1% Strain. From the stress/strain curve, the % Strain at the stress of 0.5 MPa was also reported.

A high Young's Modulus demonstrates a hard film, while a lower Young's Modulus represents a more elastic film. A high Strain demonstrates a stretchy, elastic film, while a lower Strain represents a more brittle film.

B. Procedure for Determination of Mechanical Properties of Hair Treated with Latex Compositions Hair Treatment:

A strip of regular bleached hair (from HIP, 1 cm in width, 16 cm long, about 2.0-2.5 g of hair) was treated with the latex solution or gel (0.75 g of solution/g hair). The hair was combed through until the solution was uniformly distributed over the surface of the tress. The treated was allowed to dry overnight at room temperature.

Hair Measurement:

Three-point bending measurements were conducted using a texture analyzer (Model TA-XTPlus, Texture Technologies Corporation) equipped with a hair mounting accessory as described in *J. Cosmet. Sci.*, 53, 345-362 (November/December 2002). The cantilever bending experiment consisted of the following sequence of steps: the hair tress was placed on a 2-point of 14 cm width, and the probe, representing the third point, came down at the middle of the hair tress and performed 10-mm deformations of the hair tress. The testing protocol was:

Test mode=Compression
Pre-test speed=2 mm/sec
Test speed=2 mm/sec
Post-test speed=2 mm/sec
Target mode=Distance
Distance=10 mm
Trigger type=Auto (Force)
Trigger force=1 g The maximum force, F1, needed to deform or "bend" the hair tress was recorded. The results were obtained from the average of triplicate experiments, and the results are reported from the average of the three experiments.

C. Procedure for Determination of Curl Retention in High Humidity of Hair Treated with Latex Compositions Hair Treatment:

Regular bleached hair swatch (from HIP, 14.5 cm long, about 0.5 g) was treated with a solution or gel of 2% latex polymers (0.5 g solution/g hair). The hair was combed until the solution was uniformly distributed over the hair swatch surface. The treated hair was then rolled onto a spiral rod (about 0.5 in diameter) and allowed to dry at room temperature overnight.

Curl Retention Measurement:

The coiled hair was removed from the rod and placed in the humidity chamber at 95% RH, 25° C. for 24 hours. The Curl Retention was calculated as:

$$(Lo-Lf)/(Lo-Li) \times 100$$

wherein Lo=fully extended hair length, Li=initial coiled hair length before humidity exposure, and Lf=final hair length after 24 hours exposure.

Compositions containing latex polymers were evaluated according to the methods described above. The weight of each latex polymer in the following examples is determined on a dry weight basis.

Example 1

Evaluation of Thickener in Acrylate-Polyurethane Latex Composition

Hair tresses were treated with a gel containing 1% Guar Gum (INCI name: *Cyamopsis tetragonoloba* (Guar) Gum) and 2% of Neorez R989 (INCI name: Polycarbamyl Polyglycol Ester) and Daitosol 5000AD (INCI name: Acrylates Copolymer) at 1:1 latex polymer ratio. The physical property of the hair is shown in Table 1A.

TABLE 1A

| Sample | F1 (g) |
| --- | --- |
| NO THICKENER | 588 |
| WITH THICKENER | 1163 |

Hair tresses were treated with a gel containing 1% Carbopol Ultrez-20 (INCI name: Acrylates/C10-C30 Alkyl Acrylate Crosspolymer) and 2% solutions of Luviflex Soft (INCI name: Acrylates copolymer) and Baycusan C1001 (INCI name: Polyurethane-34) at 1:1 latex polymer ratio. The physical property of the hair is shown in Table 1B.

TABLE 1B

| Sample | F1 (g) |
| --- | --- |
| NO THICKENER | 512 |
| WITH THICKENER | 1438 |

These results demonstrate that that addition of a thickener to the latex solution makes the hair stiffer, giving it more hold.

Example 2

Evaluation of High Humidity Curl Retention

Hair swatches were treated with a gel containing 1% Guar Gum and 2% Neorez R989 and Daitosol 5000AD or a gel containing 1% Carbopol Ultrez-20 and 2% Luviflex Soft and Baycusan C1001 at 1:1 latex polymer ratio. Their high humidity curl retention results are shown below in Table 2.

TABLE 2

| Sample | Curl Retention (%) |
|---|---|
| NEOREZ R989/DAITOSOL 5000AD, no thickener | 69 |
| NEOREZ R989/DAITOSOL 5000AD, with thickener | 91 |
| LUVIFLEX SOFT/BAYCUSAN C1001, no thickener | 84 |
| LUVIFLEX SOFT/BAYCUSAN C1001, with thickener | 90 |
| Commercial 1* | 57 |
| Commercial 2** | 63 |

*Main ingredients: VP/VA copolymer, polyquaternium-11, PEG 90 M, PEG-40 hydrogenated castor oil, acrylates/C10-30 alkyl acrylate crosspolymer, alcohol denatured.
**Main ingredients: Water, Acrylates/steareth-20 methacrylate crosspolymer, polyquaternium-69, PVP, sorbitol and alcohol denatured.

These results demonstrate that addition of a thickener to the latex solution improves the curl retention of the hair.

What is claimed is:

1. A hair styling composition comprising:
   (a) latex polymer A having a Young's modulus ranging from about 0.1 MPa to about 10 MPa, and a strain, under stress at 0.5 MPa, of at least about 1%, wherein latex polymer A is Acrylates copolymer, Acrylates/Ethylhexyl Acrylate copolymer, Acrylates/VA copolymer, Polyurethane-34, Polyurethane-32, or Polyurethane-48;
   (b) latex polymer B having a Young's modulus ranging from about 10 MPa to about 6 GPa, and a strain, under stress at 0.5 MPa, of less than about 5%, wherein latex polymer B is Acrylates copolymer, Polyacrylate-2 crosspolymer, Styrene/Acrylic copolymer, Polyurethane-35, Polyurethane-1, or Polycarbamyl Polyglycol Ester; and
   at least one component chosen from thickening agents;
   wherein the total combined amount of latex polymers A and B ranges from about 0.1% to about 30% by weight, relative to the weight of the composition;
   wherein the weight ratio of latex polymers A:B ranges from about 10:1 to about 1:10; and
   wherein latex polymers A and B are dispersed particles in an aqueous dispersion medium;
   with the proviso that when latex polymer A is an acrylate latex polymer, then latex polymer B is a polyurethane latex polymer; and when a latex polymer A is a polyurethane latex polymer, then latex polymer B is an acrylate latex polymer.

2. The hair styling composition of claim 1, wherein the latex polymers A and B are present in a total combined amount ranging from about 0.5% to about 10% by weight, relative to the weight of the composition.

3. The hair styling composition of claim 1, wherein latex polymers A and B are present in a total combined amount ranging from about 1% to about 5% by weight, relative to the weight of the composition.

4. The hair styling composition of claim 1, wherein latex polymers A and B are present in a total combined amount ranging from about 1% to about 3% by weight, relative to the weight of the composition.

5. The hair styling composition of claim 1, wherein latex polymers A and B are present in individual amounts ranging from about 0.05% to about 10% by weight, relative to the weight of the composition.

6. The hair styling composition of claim 1, wherein latex polymers A and B are present in individual amounts ranging from about 1% to about 15% by weight, relative to the weight of the composition.

7. The hair styling composition of claim 1, wherein the weight ratio of latex polymers A:B ranges from about 1:5 to about 5:1.

8. The hair styling composition of claim 1, wherein the weight ratio of latex polymers A:B ranges from about 1:3 to about 3:1.

9. The hair styling composition of claim 1, wherein the weight ratio of latex polymers A:B ranges from about 1:2 to about 2:1.

10. The hair styling composition of claim 1, wherein the weight ratio of latex polymers A:B is about 1:1.

11. The hair styling composition of claim 1, wherein the weight ratio of latex polymers A:B ranges from about 1:10 to about 1:1.

12. The hair styling composition of claim 1, wherein the weight ratio of latex polymers A:B ranges from about 3:1 to about 10:1.

13. The hair styling composition of claim 1, wherein the weight ratio of latex polymers A:B ranges from about 5:1 to about 10:1.

14. The hair styling composition of claim 1, wherein the at least one component chosen from thickening agents is present in a total amount ranging from about 0.1% to about 10% by weight, relative to the weight of the composition.

15. The hair styling composition of claim 1, wherein the at least one component chosen from thickening agents is present in a total amount ranging from about 1% to about 3% by weight, relative to the weight of the composition.

16. The hair styling composition of claim 1, wherein the at least one component chosen from thickening agents includes acrylates/C10-30 alkyl acrylate crosspolymer, xanthan gum, guar gum, hydroxypropyl guar, guar hydroxypropyl trimonium chloride, hydroxyethyl cellulose, hydroxypropyl cellulose and cetyl hydroxyethyl cellulose.

17. The hair styling composition of claim 1, further comprising at least one solvent.

18. A method of styling the hair, said method comprising applying to the hair a composition comprising:
   (a) latex polymer A having a Young's modulus ranging from about 0.1 MPa to about 10 MPa, and a strain, under stress at 0.5 MPa, of at least about 1%, wherein latex polymer A is Acrylates copolymer, Acrylates/Ethylhexyl Acrylate copolymer, Acrylates/VA copolymer, Polyurethane-34, Polyurethane-32, or Polyurethane-48;
   (b) latex polymer B having a Young's modulus ranging from about 10 MPa to about 6 GPa, and a strain, under stress at 0.5 MPa, of less than about 5%, wherein latex polymer B is Acrylates copolymer, Polyacrylate-2 crosspolymer, Styrene/Acrylic copolymer, Polyurethane-35, Polyurethane-1, or Polycarbamyl Polyglycol Ester; and
   at least one component chosen from thickening agents;
   wherein the total combined amount of latex polymers A and B ranges from about 0.1% to about 30% by weight, relative to the weight of the composition;
   wherein the weight ratio of latex polymers A:B ranges from about 10:1 to about 1:10; and
   wherein latex polymers A and B are dispersed particles in an aqueous dispersion medium;
   with the proviso that when latex polymer A is an acrylate latex polymer, then latex polymer B is a polyurethane latex polymer; and when a latex polymer A is a polyurethane latex polymer, then latex polymer B is an acrylate latex polymer.

19. The method according to claim 18, further comprising a step of treating the hair with heat at a temperature ranging from about 25° C. to about 250° C. before, during, or after the application of said composition.

* * * * *